(12) United States Patent
Cohen et al.

(10) Patent No.: US 6,684,105 B2
(45) Date of Patent: Jan. 27, 2004

(54) TREATMENT OF DISORDERS BY UNIDIRECTIONAL NERVE STIMULATION

(75) Inventors: Ehud Cohen, Ganei Tikva (IL); Yossi Gross, Moshav Mazor (IL)

(73) Assignee: Biocontrol Medical, Ltd., Yehud (IL)

( * ) Notice: Subject to any disclaimer, the term of this patent is extended or adjusted under 35 U.S.C. 154(b) by 71 days.

(21) Appl. No.: 09/944,913

(22) Filed: Aug. 31, 2001

(65) Prior Publication Data

US 2003/0045914 A1 Mar. 6, 2003

(51) Int. Cl.$^7$ ................................................. A61N 1/08
(52) U.S. Cl. .............................. 607/63; 607/40; 607/45; 607/46; 607/62
(58) Field of Search ................................ 607/2, 40, 46, 607/62, 63, 148, 149, 45; 600/1–3, 9–12, 26

(56) References Cited

U.S. PATENT DOCUMENTS

| | | | |
|---|---|---|---|
| 3,411,507 A | 11/1968 | Wingrove | 128/422 |
| 4,535,785 A | 8/1985 | Van Den Honert | 128/746 |
| 4,573,481 A | 3/1986 | Bullara | 128/784 |
| 4,602,624 A | 7/1986 | Naples et al. | 128/784 |
| 4,608,985 A | 9/1986 | Chrish et al. | 128/419 R |
| 4,628,942 A | 12/1986 | Sweeney et al. | 128/784 |
| 4,649,936 A * | 3/1987 | Ungar et al. | 128/784 |
| 4,702,254 A | 10/1987 | Zabara | 128/421 |
| 4,739,764 A | 4/1988 | Lue et al. | 128/419 R |
| 4,867,164 A | 9/1989 | Zabara | 128/421 |
| 4,962,751 A | 10/1990 | Krauter | 128/4 |

(List continued on next page.)

FOREIGN PATENT DOCUMENTS

WO    WO 01/10375    2/2000

OTHER PUBLICATIONS

U.S. Provisional patent application No.: 60/263,834, entitled: Selected Blocking of Nerve Fibers, filed Jan. 25, 2001.

"Generation of undirectionally propagating action potentials using a monopolar electrode cuff", Annals of Biomedical Engineering, vol. 14, pp. 437–450, 1986, By Ira J. Ungar et al.

"An asymmetric two electrode cuff for generation of undirectionally propagated action potentials", IEEE Transactions on Biomedical Engineering, vol. BME–33, No. 6, Jun. 1986, By James D. Sweeney, et al.

A spiral nerve cuff electrode for peripheral nerve stimulation, by Gregory G. Naples, et al., IEEE Transactions on Biomedical Engineering, vol. 35, No. 11, Nov. 1988.

A nerve cuff technique for selective excitation of peripheral nerve trunk regions, By James D. Sweeney, et al., IEEE Transactions on Biomedical Engineering, vol. 37, No. 7, Jul. 1990.

"Generation of undirectionally propagated action potentials in a peripheral nerve by brief stimuli", By Van Den Honert, et al., 206 Science, pp. 1311–1312, Dec. 14, 1979.

(List continued on next page.)

Primary Examiner—Mark Bockelman
(74) Attorney, Agent, or Firm—Darby & Darby

(57) ABSTRACT

Apparatus for treating a condition of a subject is provided. An electrode device is adapted to be coupled to longitudinal nervous tissue of the subject, and a control unit is adapted to drive the electrode device to apply to the nervous tissue a current which is capable of inducing action potentials that propagate in the nervous tissue in a first direction, so as to treat the condition. The control unit is further adapted to suppress action potentials from propagating in the nervous tissue in a second direction opposite to the first direction.

36 Claims, 1 Drawing Sheet

U.S. PATENT DOCUMENTS

| | | | |
|---|---|---|---|
| 5,025,807 A | 6/1991 | Zabara | 128/421 |
| 5,188,104 A | 2/1993 | Wernicke et al. | 128/419 R |
| 5,199,430 A | 4/1993 | Fang et al. | 128/419 E |
| 5,205,285 A | 4/1993 | Baker | 128/423 R |
| 5,215,086 A | 6/1993 | Terry et al. | 128/421 |
| 5,263,480 A | 11/1993 | Wernicke et al. | 607/118 |
| 5,282,468 A | 2/1994 | Klepinski | 128/642 |
| 5,292,344 A | 3/1994 | Douglas | 607/40 |
| 5,299,569 A | 4/1994 | Wernicke et al. | 607/45 |
| 5,335,657 A | 8/1994 | Terry et al. | 607/45 |
| 5,423,872 A | 6/1995 | Cigaina | 607/40 |
| 5,540,730 A | 7/1996 | Terry et al. | 607/40 |
| 5,540,734 A | 7/1996 | Zabara | 607/46 |
| 5,571,150 A | 11/1996 | Wernicke et al. | 607/72 |
| 5,690,691 A | 11/1997 | Chen | 607/40 |
| 5,707,400 A | 1/1998 | Terry et al. | 607/44 |
| 5,716,385 A | 2/1998 | Mittal et al. | 607/40 |
| 5,755,750 A * | 5/1998 | Petruska et al. | 607/75 |
| 5,836,994 A | 11/1998 | Bourgeois | 607/40 |
| 6,026,326 A | 2/2000 | Bardy | 607/40 |
| 6,058,331 A | 5/2000 | King | 607/62 |
| 6,083,249 A | 7/2000 | Familoni | 607/40 |
| 6,091,992 A | 7/2000 | Bourgeois | 399/297 |
| 6,097,984 A | 8/2000 | Douglas | 607/40 |
| 6,104,955 A | 8/2000 | Bourgeois | 607/40 |
| 6,205,359 B1 | 3/2001 | Boveja | 607/45 |
| 6,319,241 B1 * | 11/2001 | King et al. | 604/502 |

OTHER PUBLICATIONS

"A technique for collision block of peripheral nerve: Frequency dependence" Van Den Honert, C., Mortimer, J. T.: MP–12, IEEE Transactions on Biomedical Engineering, 28:379–382, 1981.

"A nerve cuff design for the selective activation and blocking of myelinated nerve fibers", D.M. Fitzpatrick, et al., Ann. Conf. Of the IEEE Engineering in Medicine and Biology Soc., vol. 13, No. 2, pp. 906, 1991.

"Orderly recruitment of motoneurons in an acute rabit model", N.J.M. Rijkhof, et al., Ann. Conf. Of the IEEE Eng., Medicine and Biology Soc., vol. 20, No. 5, pp. 2564, 1998.

"Orderly stimulation of skeletal muscle motor units with tripolar nerve cuff electrode", R. Bratta, et al., IEEE Transactions on Biomedical Engineering, vol. 36, No. 8, pp. 836, 1989.

M. Devor, "Pain Networks", Handbook of Brand Theory and Neural Networks, Ed. M.A. Arbib, MIT Press, pp. 698, 1998.

U.S. patent application No.: 09/824,682, entitled: "Method and Apparatus for selective Control of Nerve fibers", filed Apr. 4, 2001.

http://www.bcm.tmc.edu/neurol/struct/epilep/epilipsy_vagus.html. May 31, 2001.

J.F. Cortese, "Vagus Nerve Stimulation for Control of Intractable Epileptic Seizures", available at: http://www.science.wayne.edu/~bio340/StudentPages/cortese/, May 31, 2001.

* cited by examiner

TREATMENT OF DISORDERS BY UNIDIRECTIONAL NERVE STIMULATION

FIELD OF THE INVENTION

The present invention relates generally to treating patients by application of electrical signals to a selected nerve or nerve bundle, and specifically to methods and apparatus for stimulating nerve tissue while minimizing possible accompanying side effects.

BACKGROUND OF THE INVENTION

The use of nerve stimulation for treating and controlling a variety of medical, psychiatric, and neurological disorders has seen significant growth over the last several decades. In particular, stimulation of the vagus nerve (the tenth cranial nerve) has been the subject of considerable research. The vagus nerve is composed of somatic and visceral afferents (inward conducting nerve fibers, which convey impulses toward the brain) and efferents (outward conducting nerve fibers, which convey impulses to an effector to regulate activity such as muscle contraction or glandular secretion). The vagus nerve is responsible for controlling and/or receiving feedback from various glands, the pharynx, larynx, heart, lungs, liver, stomach, intestine, and ureters. Because of its large number of functions with respect to a range of body systems, the vagus nerve is preferred in many applications for purposes of modulating the functions of designated organs or portions of the central nervous system (CNS).

U.S. Pat. No. 5,540,730 to Terry et al., which is incorporated herein by reference, describes a method for treating motility disorders by applying a signal to the vagus nerve of a patient, in order to stimulate or inhibit neural impulses and produce excitatory or inhibitory neurotransmitter release by the nerve, according to the specific nature of the motility disorder.

U.S. Pat. Nos. 5,188,104 and 5,263,480 to Wernicke et al., which are incorporated herein by reference, describe a method for treating compulsive eating disorders by applying a stimulating signal to the vagus nerve of the patient appropriate to alleviate the effect of the eating disorder. For example, in cases where the disorder is compulsive eating, the stimulating signal is described as being calibrated to produce a sensation of satiety in the patient. In cases where the disorder is compulsive refusal to eat (anorexia nervosa), the stimulating signal is described as being calibrated to produce a sensation of hunger or to suppress satiety in the patient.

U.S. Pat. No. 5,571,150 to Wernicke et al., which is incorporated herein by reference, describes a method for treating a comatose patient by stimulating a cranial nerve, preferably the vagus nerve, in order to modulate the activity of the nerve in an effort to rouse the patient from the coma.

U.S. Pat. Nos. 4,702,254, 4,867,164 and 5,025,807 to Zabara, which are incorporated herein by reference, generally describe methods for controlling or preventing epileptic seizures and other motor disorders by stimulating the vagus nerve.

U.S. Pat. No. 6,205,359 to Boveja, which is incorporated herein by reference, describes apparatus for treating various forms of epilepsy and involuntary movement disorders by electrical stimulation of the left vagus nerve.

U.S. Pat. No. 5,205,285 to Baker, which is incorporated herein by reference, describes a device designed to avoid undesirable voice modulation of patients undergoing vagal stimulation therapy, while maintaining a bias in certain circumstances toward ongoing delivery of the therapy. In essence, this device requires the addition of sensing means to detect the patient's attempts at speech, responsive to which the device halts or delays the vagal stimulation during the time that speech attempts continue to be detected.

U.S. Pat. No. 5,299,569 to Wernicke et al., which is incorporated herein by reference, describes a method for treating and controlling neuropsychiatric disorders, including schizophrenia, depression and borderline personality disorder, by selectively applying a predetermined electrical signal to the patient's vagus nerve, in order to alleviate the symptoms of the disorder being treated.

U.S. Pat. No. 5,335,657 to Terry et al., which is incorporated herein by reference, describes a method for treating and controlling sleep disorders by applying an electrical signal to the vagus nerve in order to modulate electrical activity of afferent fibers of the nerve.

U.S. Pat. No. 5,707,400 to Terry et al., which is incorporated herein by reference, describes a method for treating patients suffering from refractory hypertension, also by stimulating the vagus nerve.

As is seen from this list of patents, stimulation of the nervous system, particularly the vagus nerve, for therapeutic purposes has been the subject of a considerable amount of research and application to medical, psychiatric, and neurological disorders. However, other than the problem of speech impairment addressed by the above-cited U.S. Pat. No. 5,205,285 to Baker, the possible unwanted side effects, both proven and potential, of selective stimulation of the vagus nerve, have not been given extensive consideration.

U.S. Pat. No. 5,282,468 to Klepinski, which is incorporated herein by reference, describes an implantable neural electrode.

U.S. Pat. No. 4,628,942 to Sweeney et al., which is incorporated herein by reference, describes an asymmetric, shielded, two-electrode cuff for stimulating a nerve.

U.S. Pat. No. 4,535,785 to van den Honert et al., describes implantable electronic apparatus.

U.S. Pat. No. 4,602,624 to Naples et al., which is incorporated herein by reference, describes an implantable electrode cuff for applying signals to nerves.

U.S. Pat. No. 5,199,430 to Fang et al., which is incorporated herein by reference, describes implantable electronic apparatus for assisting the urinary sphincter to relax.

U.S. Pat. No. 5,215,086 to Terry et al., which is incorporated herein by reference, describes a method for applying electrical stimulation to treat migraine headaches.

U.S. Pat. No. 5,755,750 to Petruska et al., which is incorporated herein by reference, describes a method for selectively inhibiting activity in nerve fibers.

U.S. Pat. No. 4,649,936 to Ungar et al., and U.S. Pat. No. 4,608,985 to Chrish et al., which are incorporated herein by reference, describe apparatus and methods for selectively blocking action potentials passing along a nerve trunk.

PCT Patent Publication WO 01/10375A2 to Felsen et al., which is incorporated herein by reference, describes a method for inhibiting action potential generation in nervous tissue.

The following articles may be of interest, and are incorporated herein by reference:

"Generation of unidirectionally propagating action potentials using a monopolar electrode cuff," Annals of Biomedical Engineering, vol. 14, pp. 437–450, 1986 by Ira J. Ungar et al.

"An asymmetric two electrode cuff for generation of unidirectionally propagated action potentials," IEEE Transactions on Biomedical Engineering, vol. BME-33, No. 6, June 1986 by James D. Sweeney et al.

"A spiral nerve cuff electrode for peripheral nerve stimulation," by Gregory G. Naples et al., IEEE Transactions on Biomedical Engineering, vol. 35, No. 11, November 1988.

"A nerve cuff technique for selective excitation of peripheral nerve trunk regions," by James D. Sweeney et al., IEEE Transactions on Biomedical Engineering, vol. 37, No. 7, July 1990.

"Generation of unidirectionally propagated action potentials in a peripheral nerve by brief stimuli," Science, vol. 206, pp. 1311–1312, December 1979.

"Generation of unidirectionally propagated action potentials in a peripheral nerve by brief stimuli," van den Honert et al., 206 Science 1311–1312, (Dec. 14, 1979).

"A technique for collision block of peripheral nerve: Frequency dependence," van den Honert, C., Mortimer, J. T.: MP-12, IEEE Trans. Biomed. Eng. 28:379–382, 1981.

"A technique for collision block of peripheral nerve: Single stimulus analysis," van den Honert, C., Mortimer, J. T.: MP-11, IEEE Trans. Biomed. Eng. 28:373–378, 1981.

"A Nerve Cuff Design for the Selective Activation and Blocking of Myelinated Nerve Fibers," D. M. Fitzpatrick et al., Ann. Conf. of the IEEE Eng. in Medicine and Biology Soc., Vol. 13, No. 2, pp. 906, 1991.

"Acute Animal Studies on the Use of Anodal Block to Reduce Urethral Resistance in Sacral Root Stimulation," N. J. M. Rijkhof et al., IEEE Transactions on Rehabilitation Engineering, Vol. 2, No. 2, pp. 92, 1994.

"Orderly Recruitment of Motoneurons in an Acute Rabbit Model," N. J. M. Rijkhoff et al., Ann. Conf. of the IEEE Eng., Medicine and Biology Soc., Vol. 20, No. 5, pp. 2564, 1998.

"Orderly Stimulation of Skeletal Muscle Motor Units with Tripolar Nerve Cuff Electrode," R. Bratta et al., IEEE Transactions on Biomedical Engineering, Vol. 36, No. 8, pp. 836, 1989.

U.S. Pat. No. 5,423,872 to Cigaina, which is incorporated herein by reference, describes a method for pacing the stomach in order to alter its natural rhythm. The principle espoused in Cigaina is that by altering the rhythm, one can either delay or speed up gastric emptying. Cigaina indicates that many different disorders, including gastroesophageal reflux disorder (GERD), can be treated using the rhythm altering method.

U.S. Pat. No. 5,716,385 to Mittal et al., which is incorporated herein by reference, describes a system to treat GERD by stimulating the skeletal muscle tissue of the crural diaphragm whenever myoelectric measurements made on the diaphragm are indicative of relaxation thereof. Stimulation of the diaphragm is intended to indirectly cause contraction of the lower esophageal sphincter (LES), and thereby inhibit a reflux event which is assumed to accompany relaxation of the diaphragm.

U.S. Pat. No. 6,097,984 to Douglas, which is incorporated herein by reference, discloses a system to treat GERD by continually simulating the LES of a patient in order to maintain it in a closed state, thereby preventing reflux. Stimulation is removed only when swallowing is detected, to allow food pass into the stomach.

U.S. Pat. Nos. 6,104,955, 6,091,992, and 5,836,994 to Bourgeois, U.S. Pat. No. 6,026,326 to Bardy, U.S. Pat. No. 6,083,249 to Familoni, U.S. Pat. No. 5,690,691 to Chen, U.S. Pat. No. 5,292,344 to Douglas, and U.S. Pat. No. 3,411,507 to Wingrove, which are incorporated herein by reference, describe methods and apparatus for electrical simulation of the GI tract to treat various physiological disorders.

SUMMARY OF THE INVENTION

It is an object of some aspects of the present invention to provide apparatus and methods for treating and controlling a medical condition by application of electrical signals to a selected nerve or nerve bundle.

It is also an object of some aspects of the present invention to provide apparatus and methods for treating and controlling a medical condition by application of electrical signals to a selected nerve or nerve bundle while minimizing adverse side effects.

It is a further object of some aspects of the present invention to provide apparatus and methods for treatment of sleep disorders while minimizing adverse side effects.

It is still a further object of some aspects of the present invention to provide apparatus and methods for treatment of neuropsychiatric disorders while minimizing adverse side effects.

It is yet a further object of some aspects of the present invention to provide apparatus and methods for treatment of eating disorders, while minimizing adverse side effects caused by stimulation of the nerves controlling the digestive system.

It is an additional object of some aspects of the present invention to provide apparatus and methods for treatment of motility disorders, while minimizing undesired side effects caused by stimulation of the nerves controlling the digestive system.

It is yet an additional object of some aspects of the present invention to provide apparatus and methods for rousing comatose patients, while minimizing adverse effects upon physiological functions.

It is still an additional object of some aspects of the present invention to provide apparatus and methods for treating epilepsy and involuntary movement disorders while minimizing unwanted side effects such as impairment of speech.

It is also an object of some aspects of the present invention to provide apparatus and methods for treating hypertension while minimizing unwanted side effects.

In preferred embodiments of the present invention, apparatus for treating a specific condition comprises a set of one or more electrode devices that are applied to one or more selected sites of the central or peripheral nervous system of a patient. A control unit preferably drives the electrode devices to: (a) apply signals which induce the propagation of nerve impulses in a desired direction in order to treat the condition, and (b) suppress artificially-induced nerve impulses in the opposite direction in order to minimize adverse side effects of the signal application.

For some applications of the present invention, the signal is applied to a nerve such as the vagus nerve, in order to stimulate efferent fibers and increase the motor activity of the small intestine and colon, and thereby treat motility disorders. Simultaneously, action potential propagation is inhibited in afferent fibers responsive to the application of the signals. In the prior art, such as that described in the above-cited U.S. Pat. No. 5,540,730 to Terry et al., the vagus nerve is stimulated so as to influence the motor activity of the small intestine and colon. However, an unintended result of applying the method of the Terry patent is that, when the nerve is stimulated, action potentials are induced in both directions (stimulating afferent and efferent fibers). Stimulation of the vagus nerve as a whole may thus produce undesired afferent stimulation, which may in turn result in, for example, the initiation of undesired or counterproductive feedback to the brain, and resultant undesired sensations or activity of the digestive system (e.g., nausea). Advantageously, and unlike the prior art, application of these embodiments of the present invention substantially stimulates only the intended efferent fibers, and reduces or eliminates the transmission of sensory signals to the CNS that could cause such undesirable responses in the digestive system.

For some applications of the present invention, the signal is applied to a portion of the vagus nerve innervating the stomach in order to stimulate sensory fibers and thereby produce a sensation, e.g., satiety or hunger. In the prior art, such as that described in the above-cited U.S. Pat. No. 5,263,480 to Wernicke et al., the vagus nerve is stimulated so as to induce certain sensory messages to propagate to the brain. However, upon the application of stimulation as described by Wernicke, action potentials are induced in both directions—on afferent and efferent fibers—and may thus generate unwanted effector responses. Depending upon the location on the vagus nerve at which stimulation is applied, such impulses may, for example, stimulate the glands of the stomach to secrete excessive hydrochloric acid, or they may reduce or otherwise affect the heartbeat of the patient. Unlike the prior art, application of this embodiment of the present invention generates substantially only sensory signals, and generally does not cause efferent signals to be transmitted to the effectors that could result in such undesirable responses.

For some applications, the signal is applied to the vagus nerve so as to modulate electrical activity in the brain, and thereby rouse a patient from a comatose condition. At the same time, the electrode devices are driven to inhibit action potentials in efferent fibers which would generally arise as a result of the application of the signal. In the prior art, such as that described in U.S. Pat. No. 5,571,150 to Wernicke et al., the vagus nerve in the neck is stimulated so as to cause afferent nerve fibers to conduct modified electrical patterns toward the reticular formation. However, inadvertent stimulation of efferent fibers resulting from the bi-directional nature of artificial nerve stimulation may result in undesirable motor, glandular or cardiac activity. Unlike the prior art, this application of the present invention inhibits action potentials in the efferent fibers, and consequently generally does not cause unwanted efferents to be generated.

Alternatively, the signal is applied to the vagus nerve to treat epilepsy and involuntary movement disorders, while action potential propagation responsive to the signal in efferent fibers is suppressed. In the prior art, either the left or right vagus nerve is stimulated as described in the above-cited Zabara and Boveja patents. The basic premise of vagal nerve stimulation for control of epileptic seizures is that vagal afferents have a diffuse central nervous system (CNS) projection, and activation of these pathways has a widespread effect on neuronal excitability. However, the mechanism by which vagal stimulation exerts its influence on seizures is not well understood.

The inventors of the present invention believe that the techniques described in the Zabara and Boveja patents induce unintended and, at least to some extent, undesirable accompanying effects resulting from the stimulation of efferent fibers at the same time as the treatment is being applied. It is well known, for example, that stimulation of the right vagus can lead to profound bradycardia (slowing of the heartbeat), which is an unwanted and unnecessary complication. Additionally, it has been determined that a side effect of vagal stimulation in epileptic patients is the presence of a noticeable modulation or reduction of the patient's voice when he or she tries to speak during application of the stimulating signals to the nerve. U.S. Pat. No. 5,205,285 to Baker, cited above, addresses the problem of voice modulation, but requires the addition of a sensor to detect the patient's speech and simply terminates the vagal stimulation, i.e., the desired treatment, whenever speech attempts continue to be detected. A drawback of this solution is that beneficial therapy may be unduly inhibited in favor of cosmetic or secondary considerations. Unlike the limitations of the prior art, however, application of this embodiment of the present invention substantially precludes the onset of these accompanying effects by permitting nerve impulses to travel only in the desired direction.

For some applications of the present invention, the signal is applied to the vagus nerve in order to treat and control sleep disorders or hypertension, while inhibiting action potential propagation in efferent fibers responsive to the applied signal. In the prior art, such as that described in U.S. Pat. Nos. 5,335,657 and 5,707,400 to Terry et al., bi-directional impulses are generated by the stimulation, resulting in both the desired treatment as well as unintended and not necessarily beneficial accompanying physiological responses. Unlike the prior art, however, application of this embodiment of the present invention substantially does not stimulate electrical activity of efferent fibers that may generate unwanted visceral, glandular, or motor responses.

In summary, the stimulation of nerve impulses in one direction while suppressing impulses in the opposite direction is preferably used to obtain the benefits of various new or prior art therapeutic treatments, including, but not limited to, those described in the references cited herein, while reducing or eliminating adverse and/or unintended side effects.

There is therefore provided, in accordance with a preferred embodiment of the present invention, a method for treating a condition of a subject, including:

driving into longitudinal nervous tissue of the subject a current which is capable of inducing action potentials that propagate in the nervous tissue in a first direction, so as to treat the condition; and suppressing action potentials from propagating in the nervous tissue in a second direction opposite to the first direction.

Preferably, driving the current includes driving a current capable of inducing action potentials that propagate in the nervous tissue in an afferent direction with respect to the central nervous system of the subject. Alternatively, driving the current includes driving a current capable of inducing action potentials that propagate in the nervous tissue in an efferent direction with respect to the central nervous system of the subject.

Driving the current typically, but not necessarily, includes driving the current into a vagus nerve of the subject.

In a preferred embodiment, the method includes driving the current and suppressing the action potentials at substantially the same time.

For some applications, driving the current includes configuring the current to be capable of treating an involuntary movement disorder of the subject.

In a preferred embodiment, suppressing the action potentials includes regulating the suppressing of the action potentials so as to inhibit an undesired response of the central nervous system of the subject generated responsive to driving the current into the nervous tissue. For example, suppressing the action potentials may include regulating the suppressing of the action potentials so as to inhibit an undesired sensation generated responsive to driving the current into the nervous tissue.

Suppressing the action potentials typically includes suppressing action potentials induced responsive to driving the current.

As appropriate, driving the current may include configuring the current to be capable of treating one or more of the following exemplary conditions of the subject: a sleep disorder, a gastrointestinal motility disorder, an eating disorder, obesity, anorexia, a gastrointestinal tract disorder, hypertension, coma, or epilepsy. During epilepsy treatment, suppressing the action potentials typically includes suppressing action potentials that interfere with an ability of the subject to speak.

In a preferred embodiment, driving the current includes applying to a vagus nerve of the subject a current capable of inducing constriction of a lower esophageal sphincter of the subject.

Typically, suppressing the action potentials includes suppressing the action potentials repeatedly, during a series of temporally non-contiguous "action potential suppression periods." The method in this case preferably includes substantially withholding the suppressing of action potentials between the action potential suppression periods.

As appropriate, driving the current may include driving the current into nervous tissue of the central nervous system of the subject and/or into nervous tissue of the peripheral nervous system of the subject.

For some applications, suppressing the action potentials includes identifying an action potential conduction velocity and suppressing action potentials characterized by the identified conduction velocity. In this case, the method preferably includes withholding suppression of an action potential having a conduction velocity substantially different from the identified conduction velocity.

In some preferred embodiments of the present invention, suppressing the action potentials includes regulating the suppressing of the action potentials so as to inhibit an undesired effector action responsive to driving the current into the nervous tissue. For example, suppressing the action potentials may include suppressing generation of action potentials that induce: (a) increased acid secretion in a gastrointestinal tract of the subject, (b) muscular contraction, and/or (c) bradycardia.

Preferably, suppressing the action potentials includes applying an electric field to the nervous tissue. Further preferably, applying the field includes applying a plurality of electric fields to the nervous tissue at respective longitudinal sites thereof. Applying the plurality of electric fields to the nervous tissue typically includes applying each of the fields at a different respective time. Moreover, applying the fields at the respective longitudinal sites typically includes applying the fields at two adjacent sites separated by at least about 2 mm. Alternatively or additionally, applying the fields at the respective longitudinal sites includes applying the fields at two adjacent sites separated by less than about 4 mm.

In a preferred embodiment, the method includes sensing an indication of a presence of the condition, and driving the current includes driving the current responsive to sensing the indication. Alternatively or additionally, the method includes receiving an input from the subject, and driving the current includes driving the current responsive to receiving the input.

There is also provided, in accordance with a preferred embodiment of the present invention, apparatus for treating a condition of a subject, including:

an electrode device, adapted to be coupled to longitudinal nervous tissue of the subject; and a control unit, adapted to drive the electrode device to apply to the nervous tissue a current which is capable of inducing action potentials that propagate in the nervous tissue in a first direction, so as to treat the condition, and adapted to suppress action potentials from propagating in the nervous tissue in a second direction opposite to the first direction.

The present invention will be more fully understood from the following detailed description of the preferred embodiment thereof, taken together with the drawings, in which:

DETAILED DESCRIPTION OF PREFERRED EMBODIMENTS

Figure 1:
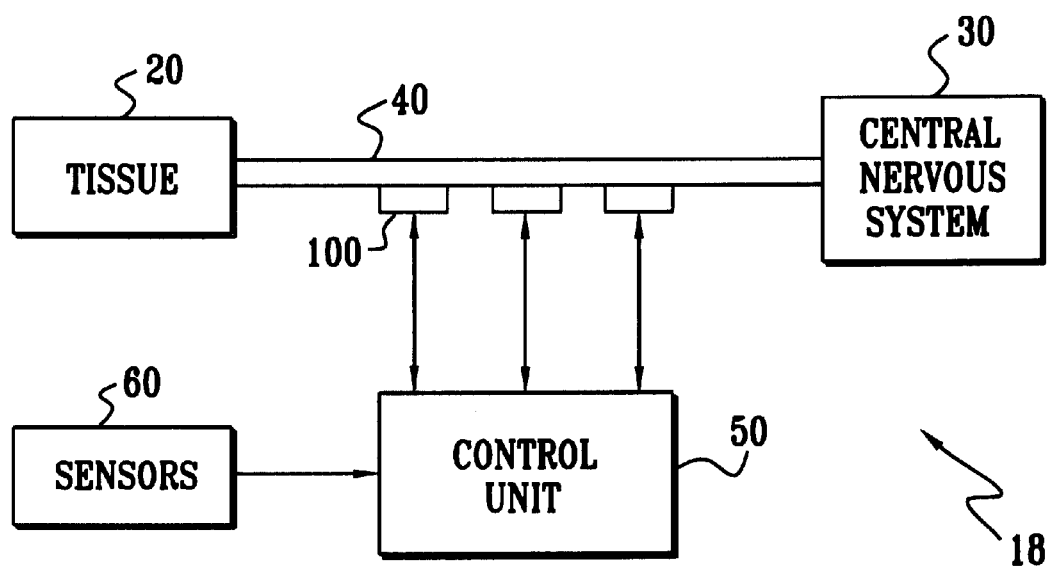
FIG. 1 is a schematic illustration of a nerve, showing the placement of electrode devices thereon, in accordance with a preferred embodiment of the present invention.

FIG. 1 is a schematic illustration of nerve stimulation apparatus 18, for applying electrical energy to induce propagation of impulses in one direction in a nerve 40, in order to treat a condition, while suppressing action potential propagation in the other direction, in accordance with a preferred embodiment of the present invention. For illustrative purposes, nerve 40 may be a cranial nerve, such as the vagus nerve, which emanates from the nervous tissue of the central nervous system (CNS) 30 and transmits sensory signals to CNS 30 and motor or other effector signals to tissue 20. Apparatus 18 typically comprises an implantable or external control unit 50, which drives one or more electrode devices 100 to apply an appropriate signal to respective sites on nerve 40. It is to be understood that whereas preferred embodiments of the present invention are described herein with respect to controlling propagation in a nerve, the scope of the present invention includes applying signals to other nervous tissue, such as individual axons or nerve tracts.

Preferably, control unit 50 receives and analyzes signals from sensors 60 located at selected sites in, on, or near the body of the patient. These sensor signals are typically qualitative and/or quantitative measurements of a medical, psychiatric and/or neurological characteristic of a disorder being treated. For example, sensors 60 may comprise electroencephalographic (EEG) apparatus to detect the onset of a seizure, or a user input unit, adapted to receive an indication of a level of discomfort, hunger, or fatigue experienced by the patient. Preferably, the sensor signals are analyzed within control unit 50, which, responsive to the analysis, drives electrode devices 100 to apply current to one or more sites on nerve 40, configured such that application thereof stimulates unidirectional propagation of nerve impulses to treat the specific disorder of the patient.

Alternatively, nerve stimulation apparatus 18 operates without sensors 60. In such a preferred embodiment, control unit 50 is typically preprogrammed to operate continuously, in accordance with a schedule, or under regulation by an external source.

For some applications of the present invention, the signals applied by control unit 50 to electrode devices 100 are configured to induce efferent nerve impulses (i.e., action potentials propagating in the direction of tissue 20), while suppressing nerve impulses traveling in nerve 40 towards CNS 30. For illustrative purposes, tissue 20 may comprise muscle tissue of the gastrointestinal tract, and treatment of motility disorders may be accomplished by inducing propagation of nerve impulses towards the muscle tissue, while suppressing the propagation of nerve impulses to CNS 30. Preferably, methods and apparatus described in U.S. Pat. No. 5,540,730 to Terry et al. are adapted for use with this embodiment of the present invention. In contrast to the outcome of application of the apparatus described in the Terry patent, however, in this embodiment of the present invention, CNS 30 substantially does not receive sensory signals that could potentially generate undesired responses.

Alternatively or additionally, gastroesophageal reflux disease (GERD) is treated by stimulating the vagus nerve unidirectionally, in order to induce constriction of the lower esophageal sphincter. Advantageously, such an application of unidirectional stimulation inhibits or substantially eliminates undesired sensations or other feedback to the central nervous system which would in some cases be induced responsive to stimulation of the vagus nerve. It is noted that this suppression of afferent impulses is typically only applied during the relatively short time periods during which pulses are applied to the vagus nerve, such that normal, physiological afferent impulses are in general able to travel, uninhibited, towards the CNS. For some applications, apparatus and methods described in the above-cited U.S. Pat. Nos. 5,188,104, 5,716,385 or 5,423,872 are adapted for use with unidirectional stimulation as provided by this embodiment of the present invention.

For some applications of the present invention, electrode devices 100 are configured to induce afferent impulses (i.e., action potentials propagating in the direction of CNS 30), while suppressing impulses in the direction of tissue 20. Typically, conditions such as eating disorders, coma, epilepsy, motor disorders, sleep disorders, hypertension, and neuropsychiatric disorders are treated by adapting techniques described in one or more of the above-cited references for use with therapeutic unidirectional impulse generation as provided by these embodiments of the present invention. Advantageously, this avoids unwanted and not necessarily beneficial outcomes of the prior art technique, such as bradycardia, enhanced gastric acid secretion, or other effects secondary to stimulation of the vagus nerve and communication of unintended nerve impulses to tissue 20. Which specific tissue 20 receives the efferent stimulation unintentionally induced by the prior art techniques depends upon the location on the nerve at which the stimulation is applied. For example, branchial motor efferents of the vagus nerve supply the voluntary muscles of the pharynx and most of the larynx, as well as one muscle of the tongue. The visceral efferents include parasympathetic innervation of the smooth muscle and glands of the pharynx, larynx, and viscera of the thorax and abdomen. Consequently, unintended efferent signal generation may induce undesired or unexpected responses in any of the tissue controlled and regulated by the vagus nerve. In preferred embodiments of the present invention, by contrast, such responses are suppressed while, at the same time, the desired afferent nerve signals are transmitted to CNS 30.

A variety of methods for inducing unidirectional propagation of action potentials are known in the art, some of which are described in the references cited in the Background section of the present patent application and may be adapted for use with preferred embodiments of the present invention.

In a preferred embodiment, unidirectional signal propagation is induced using methods and apparatus disclosed in:

U.S. Provisional Patent Application 60/263,834 to Cohen and Ayal, filed Jan. 25, 2001, entitled "Selective blocking of nerve fibers," which is assigned to the assignee of the present patent application and is incorporated herein by reference, U.S. patent application Ser. No. 09/824,682, filed Apr. 4, 2001, entitled "Method and apparatus for selective control of nerve fibers," to Cohen and Ayal, which is assigned to the assignee of the present patent application and is incorporated herein by reference, and/or the above-cited U.S. Pat. No. 5,199,430, 4,628,942, and/or 4,649,936.

The Cohen and Ayal regular patent application describes a method for:

(a) selectively suppressing the propagation of naturally-generated action potentials which propagate in a predetermined direction at a first conduction velocity through a first group of nerve fibers in a nerve bundle, while (b) avoiding unduly suppressing the propagation of naturally-generated action potentials propagated in the predetermined direction at a different conduction velocity through a second group of nerve fibers in the nerve bundle.

The method includes applying a plurality of electrode devices to the nerve bundle, spaced at intervals along the bundle. Each electrode device is capable of inducing, when actuated, unidirectional "electrode-generated" action potentials, which produce collision blocks with respect to the naturally-generated action potentials propagated through the second group of nerve fibers. Moreover, each electrode device is actuated in sequence, with inter-device delays timed to generally match the first conduction velocity and to thereby produce a wave of anodal blocks, which: (a) minimize undesired blocking of the naturally-generated action potentials propagated through the first group of nerve fibers, while (b) maximizing the generation rate of the unidirectional electrode-generated action potentials which produce collision blocks of the naturally-generated action potentials propagated through the second group of nerve fibers. Such a method may be used for producing collision blocks in sensory nerve fibers in order to suppress pain, and also in motor nerve fibers to suppress selected muscular or glandular activities.

Alternatively or additionally, embodiments of the present invention induce the propagation of unidirectional action potentials using techniques described in the above-cited U.S. Pat. No. 4,649,936 to Ungar et al., and U.S. Pat. No. 4,608,985 to Chrish et al., which describe apparatus and methods for selectively blocking action potentials passing along a nerve trunk. In this case, electrode device 100 comprises an asymmetric, single electrode cuff, which includes an electrically non-conductive or dielectric sleeve that defines an axial passage therethrough. The dielectric sheath and axial passage extend from a first end, which is disposed toward the origin of orthodromic pulses, to a second end. The gap between the nerve and the cuff is filled by conductive body tissues and fluids after implantation in the body. A single annular electrode is disposed in the axial passage, which may be mounted on the inner surface of the dielectric sleeve within the axial passage. Other implementation details may be found in the Ungar and Chrish patents.

It is to be understood that whereas preferred embodiments of the present invention are generally described hereinabove with respect to stimulating and inhibiting action potential propagation in the vagus nerve, the scope of the present invention includes applying analogous techniques to other central or peripheral nervous tissue of a patient.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. A method for treating a condition of a subject, comprising:
   driving into longitudinal nervous tissue of the subject a current which is capable of inducing action potentials that propagate in the nervous tissue in an orthodromic direction, so as to treat the condition; and
   suppressing action potentials from propagating in the nervous tissue in an antidromic direction.

2. A method according to claim 1, wherein driving the current comprises driving a current capable of inducing action potentials that propagate in the nervous tissue in an afferent direction with respect to the central nervous system of the subject.

3. A method according to claim 1, wherein driving the current comprises driving a current capable of inducing action potentials that propagate in the nervous tissue in an efferent direction with respect to the central nervous system of the subject.

4. A method according to claim 1, wherein driving the current comprises driving the current into a vagus nerve of the subject.

5. A method according to claim 1, wherein the method comprises driving the current and suppressing the action potentials at substantially the same time.

6. A method according to claim 1, wherein driving the current comprises configuring the current to be capable of treating an involuntary movement disorder of the subject.

7. A method according to claim 1, wherein suppressing the action potentials comprises regulating the suppressing of the action potentials so as to inhibit an undesired response of the central nervous system of the subject generated responsive to driving the current into the nervous tissue.

8. A method according to claim 1, wherein suppressing the action potentials comprises regulating the suppressing of the action potentials so as to inhibit an undesired sensation generated responsive to driving the current into the nervous tissue.

9. A method according to claim 1, wherein suppressing the action potentials comprises suppressing action potentials induced responsive to driving the current.

10. A method according to claim 1, wherein driving the current comprises configuring the current to be capable of treating a sleep disorder of the subject.

11. A method according to claim 1, wherein driving the current comprises configuring the current to be capable of treating a gastrointestinal motility disorder of the subject.

12. A method according to claim 1, wherein driving the current comprises configuring the current to be capable of treating an eating disorder of the subject.

13. A method according to claim 1, wherein driving the current comprises configuring the current to be capable of treating obesity of the subject.

14. A method according to claim 1, wherein driving the current comprises configuring the current to be capable of treating anorexia of the subject.

15. A method according to claim 1, wherein driving the current comprises configuring the current to be capable of treating a gastrointestinal tract disorder of the subject.

16. A method according to claim 1, wherein driving the current comprises configuring the current to be capable of treating hypertension of the subject.

17. A method according to claim 1, wherein driving the current comprises configuring the current to be capable of treating coma of the subject.

18. A method according to claim 1, wherein driving the current comprises configuring the current to be capable of treating epilepsy of the subject.

19. A method according to claim 1, wherein driving the current comprises driving the current into a vagus nerve of the subject and configuring the current to be capable of treating epilepsy of the subject, and wherein suppressing the action potentials comprises suppressing action potentials that interfere with an ability of the subject to speak.

20. A method according to claim 1, wherein driving the current comprises applying to a vagus nerve of the subject a current capable of inducing constriction of a lower esophageal sphincter of the subject.

21. A method according to claim 1, wherein suppressing the action potentials comprises suppressing the action potentials repeatedly, during a series of temporally non-contiguous action potential suppression periods, and wherein the method comprises substantially withholding the suppressing of action potentials between the action potential suppression periods.

22. A method according to claim 1, wherein driving the current comprises driving the current into nervous tissue of the central nervous system of the subject.

23. A method according to claim 1, wherein driving the current comprises driving the current into nervous tissue of the peripheral nervous system of the subject.

24. A method according to claim 1, wherein suppressing the action potentials comprises identifying an action potential conduction velocity and suppressing action potentials characterized by the identified conduction velocity.

25. A method according to claim 24, wherein the method comprises withholding suppression of an action potential having a conduction velocity substantially different from the identified conduction velocity.

26. A method according to claim 1, wherein suppressing the action potentials comprises regulating the suppressing of the action potentials so as to inhibit an undesired effector action responsive to driving the current into the nervous tissue.

27. A method according to claim 26, wherein suppressing the action potentials comprises suppressing generation of action potentials that induce increased acid secretion in a gastrointestinal tract of the subject.

28. A method according to claim 26, wherein suppressing the action potentials comprises suppressing generation of action potentials that induce muscular contraction.

29. A method according to claim 26, wherein suppressing the action potentials comprises suppressing generation of action potentials that induce bradycardia.

30. A method according to claim 1, wherein suppressing the action potentials comprises applying an electric field to the nervous tissue.

31. A method according to claim 30, wherein applying the field comprises applying a plurality of electric fields to the nervous tissue at respective longitudinal sites thereof.

32. A method according to claim 31, wherein applying the plurality of electric fields to the nervous tissue comprises applying each of the fields at a different respective time.

33. A method according to claim 31, wherein applying the fields at the respective longitudinal sites comprises applying the fields at two adjacent sites separated by at least about 2 mm.

34. A method according to claim 31, wherein applying the fields at the respective longitudinal sites comprises applying the fields at two adjacent sites separated by less than about 4 mm.

35. A method according to claim 1, and comprising sensing an indication of a presence of the condition, wherein driving the current comprises driving the current responsive to sensing the indication.

36. A method according to claim 1, and comprising receiving an input from the subject, wherein driving the current comprises driving the current responsive to receiving the input.

* * * * *